(12) United States Patent
Rule et al.

(10) Patent No.: US 7,993,308 B2
(45) Date of Patent: Aug. 9, 2011

(54) ULTRASOUND ENHANCED CENTRAL VENOUS CATHETER

(75) Inventors: Peter R. Rule, Los Altos, CA (US); Douglas R. Hansmann, Bainbridge Island, WA (US); Dominic D. Vogt, Redmond, WA (US); Curtis Genstler, Snohomish, WA (US); Thomas O. McNamara, Los Angeles, CA (US)

(73) Assignee: Ekos Corporation, Bothell, WA (US)

( * ) Notice: Subject to any disclaimer, the term of this patent is extended or adjusted under 35 U.S.C. 154(b) by 1868 days.

(21) Appl. No.: 11/046,052

(22) Filed: Jan. 28, 2005

(65) Prior Publication Data

US 2005/0197619 A1 Sep. 8, 2005

Related U.S. Application Data

(63) Continuation of application No. 10/828,938, filed on Apr. 21, 2004, now abandoned.

(60) Provisional application No. 60/464,673, filed on Apr. 22, 2003.

(51) Int. Cl.
*A61M 25/00* (2006.01)

(52) U.S. Cl. ...................................... 604/266

(58) Field of Classification Search .............. 604/19–22, 604/264–271; 601/2; 600/114
See application file for complete search history.

(56) References Cited

U.S. PATENT DOCUMENTS

| 3,433,226 A | 3/1969 | Boyd |
| 4,040,414 A | 8/1977 | Suroff |
| 4,176,662 A | 12/1979 | Frazer |
| 4,319,580 A | 3/1982 | Colley |
| 4,531,943 A | 7/1985 | Van Tassel |
| 4,549,533 A | 10/1985 | Cain et al. |
| 4,698,058 A | 10/1987 | Greenfeld et al. |
| 4,739,768 A | 4/1988 | Engelson |

(Continued)

FOREIGN PATENT DOCUMENTS

DE 40 05 743 8/1991

(Continued)

OTHER PUBLICATIONS

Hynynen et al.; "Small Cylindrical Ultrasound Sources for Induction of Hyperthermia Via Body Cavities or Interstitial Implants", Arizona Cancer Center and Department of Radiation Oncology, University of Arizona Health Sciences Center; vol. 9, No. 2; pp. 263-274; 1993.

(Continued)

*Primary Examiner* — Manuel A Mendez
(74) *Attorney, Agent, or Firm* — Knobbe, Martens, Olson & Bear, LLP

(57) ABSTRACT

A central venous catheter comprises an ultrasound assembly. In one arrangement, the radiating member is used to remove a blockage from the central venous catheter. In another arrangement, inserting an ultrasound assembly into a central venous catheter. The ultrasound assembly comprises an ultrasound radiating member mounted on an elongate support structure. The method further comprises positioning the ultrasound assembly within the central venous catheter such that the ultrasound radiating member is adjacent to a deposited material formed on a portion of the central venous catheter. The method further comprises supplying an electrical current to the ultrasound radiating member to expose the deposited material to ultrasonic energy. The method further comprises passing a therapeutic compound through the central venous catheter to expose the deposited material to the therapeutic compound simultaneously with ultrasonic energy.

20 Claims, 6 Drawing Sheets

U.S. PATENT DOCUMENTS

| | | | |
|---|---|---|---|
| 4,750,902 A | 6/1988 | Wuchinich | |
| 4,808,153 A | 2/1989 | Parisi | |
| 4,841,977 A | 6/1989 | Griffith et al. | |
| 4,870,953 A | 10/1989 | Donmicheal | |
| 4,906,238 A | 3/1990 | Greenfeld et al. | |
| 4,920,954 A | 5/1990 | Alliger | |
| 4,924,863 A | 5/1990 | Sterzer | |
| 4,936,281 A | 6/1990 | Stasz | |
| 4,948,587 A | 8/1990 | Kost et al. | |
| 5,021,044 A | 6/1991 | Sharkawy | |
| 5,059,851 A | 10/1991 | Corl et al. | |
| 5,108,369 A | 4/1992 | Ganguly et al. | |
| 5,158,071 A | 10/1992 | Umemura et al. | |
| 5,163,421 A | 11/1992 | Bernstein et al. | |
| 5,197,946 A | 3/1993 | Tachibana | |
| 5,226,421 A | 7/1993 | Frisbie et al. | |
| 5,250,034 A | 10/1993 | Appling | |
| 5,267,954 A | 12/1993 | Nita | |
| 5,267,985 A | 12/1993 | Shimada | |
| 5,269,291 A | 12/1993 | Carter | |
| 5,269,297 A | 12/1993 | Weng et al. | |
| 5,271,406 A | 12/1993 | Ganguly et al. | |
| 5,282,785 A | 2/1994 | Shapland et al. | |
| 5,286,254 A | 2/1994 | Shapland | |
| 5,295,484 A | 3/1994 | Marcus | |
| 5,304,115 A | 4/1994 | Pflueger et al. | |
| 5,312,328 A | 5/1994 | Nita et al. | |
| 5,318,014 A | 6/1994 | Carter | |
| 5,327,891 A | 7/1994 | Rammler | |
| 5,328,470 A | 7/1994 | Nabel | |
| 5,342,292 A | 8/1994 | Nita et al. | |
| 5,344,435 A | 9/1994 | Turner | |
| 5,345,940 A | 9/1994 | Seward et al. | |
| 5,353,798 A | 10/1994 | Sieben | |
| 5,354,279 A | 10/1994 | Hofling | |
| 5,362,309 A | 11/1994 | Carter | |
| 5,368,036 A | 11/1994 | Tanaka et al. | |
| 5,368,557 A | 11/1994 | Nita et al. | |
| 5,380,273 A | 1/1995 | Dubrul et al. | |
| 5,382,228 A | 1/1995 | Nita et al. | |
| 5,385,148 A | 1/1995 | Lesh et al. | |
| 5,421,338 A | 6/1995 | Crowley | |
| 5,423,797 A | 6/1995 | Adrian et al. | |
| 5,427,118 A | 6/1995 | Nita et al. | |
| 5,429,136 A | 7/1995 | Milo et al. | |
| 5,445,155 A | 8/1995 | Sieben | |
| 5,447,509 A | 9/1995 | Mills et al. | |
| 5,447,510 A | 9/1995 | Jensen | |
| 5,454,795 A | 10/1995 | Samson | |
| 5,458,568 A | 10/1995 | Racchini | |
| 5,462,523 A | 10/1995 | Samson | |
| 5,465,726 A | 11/1995 | Dickinson | |
| 5,474,531 A | 12/1995 | Carter | |
| 5,496,267 A | 3/1996 | Drasler et al. | |
| 5,496,294 A | 3/1996 | Hergenrother et al. | |
| 5,498,238 A | 3/1996 | Shapland | |
| 5,503,155 A | 4/1996 | Salmon et al. | |
| 5,514,092 A | 5/1996 | Forman | |
| 5,520,189 A | 5/1996 | Malinowski | |
| 5,531,715 A | 7/1996 | Engelson et al. | |
| 5,533,986 A | 7/1996 | Mottola et al. | |
| 5,542,917 A | 8/1996 | Nita et al. | |
| 5,560,362 A | 10/1996 | Sliwa, Jr. et al. | |
| 5,569,197 A | 10/1996 | Helmus et al. | |
| 5,571,086 A | 11/1996 | Kaplan et al. | |
| 5,588,432 A | 12/1996 | Crowley | |
| 5,599,326 A | 2/1997 | Carter | |
| 5,603,694 A | 2/1997 | Brown et al. | |
| 5,606,974 A | 3/1997 | Castellano | |
| 5,609,574 A | 3/1997 | Kaplan et al. | |
| 5,620,479 A | 4/1997 | Diederich | |
| 5,628,728 A | 5/1997 | Tachibana et al. | |
| 5,628,730 A | 5/1997 | Shapland | |
| 5,630,837 A | 5/1997 | Crowley | |
| 5,713,848 A | 2/1998 | Dubrul et al. | |
| 5,725,494 A * | 3/1998 | Brisken | 604/22 |
| 5,728,062 A | 3/1998 | Brisken | |
| 5,735,811 A | 4/1998 | Brisken | |
| 5,782,811 A | 7/1998 | Samson et al. | |
| 5,807,395 A | 9/1998 | Mulier et al. | |
| 5,827,529 A | 10/1998 | Ono et al. | |
| 5,830,127 A * | 11/1998 | DeCastro | 600/157 |
| 5,836,896 A | 11/1998 | Rosenschein | |
| 5,836,946 A | 11/1998 | Diaz et al. | |
| 5,842,994 A | 12/1998 | TenHoff et al. | |
| 5,895,398 A | 4/1999 | Wensel et al. | |
| 5,916,192 A | 6/1999 | Nita et al. | |
| 5,928,186 A | 7/1999 | Homsma et al. | |
| 5,931,805 A | 8/1999 | Brisken | |
| 5,951,494 A | 9/1999 | Wang et al. | |
| 5,971,949 A | 10/1999 | Levin et al. | |
| 5,976,120 A | 11/1999 | Chow et al. | |
| 5,997,497 A | 12/1999 | Nita et al. | |
| 6,001,069 A * | 12/1999 | Tachibana et al. | 601/2 |
| 6,024,703 A | 2/2000 | Zanelli et al. | |
| 6,024,718 A | 2/2000 | Chen et al. | |
| 6,053,868 A | 4/2000 | Geistert et al. | |
| 6,096,000 A | 8/2000 | Tachibana et al. | |
| 6,110,314 A | 8/2000 | Nix et al. | |
| 6,113,558 A | 9/2000 | Rosenschein et al. | |
| 6,120,454 A | 9/2000 | Suorsa et al. | |
| 6,135,971 A | 10/2000 | Hutchinson et al. | |
| 6,143,013 A | 11/2000 | Samson et al. | |
| 6,176,842 B1 | 1/2001 | Tachibana et al. | |
| 6,182,666 B1 | 2/2001 | Dobak, III | |
| 6,206,831 B1 | 3/2001 | Suorsa et al. | |
| 6,210,356 B1 | 4/2001 | Anderson et al. | |
| 6,228,046 B1 | 5/2001 | Brisken | |
| 6,234,958 B1 * | 5/2001 | Snoke et al. | 600/114 |
| 6,235,024 B1 | 5/2001 | Tu | |
| 6,241,703 B1 | 6/2001 | Levin et al. | |
| 6,287,271 B1 | 9/2001 | Dubrul et al. | |
| 6,296,619 B1 | 10/2001 | Brisken et al. | |
| 6,361,500 B1 | 3/2002 | Masters | |
| 6,361,531 B1 | 3/2002 | Hissong | |
| 6,368,315 B1 | 4/2002 | Gillis et al. | |
| 6,372,498 B2 | 4/2002 | Newman et al. | |
| 6,379,320 B1 | 4/2002 | Lafon et al. | |
| 6,387,035 B1 | 5/2002 | Jung, Jr. et al. | |
| 6,423,026 B1 | 7/2002 | Gesswein et al. | |
| 6,433,464 B2 | 8/2002 | Jones | |
| 6,437,487 B1 | 8/2002 | Mohr, III et al. | |
| 6,461,314 B1 | 10/2002 | Pant et al. | |
| 6,508,775 B2 | 1/2003 | McKenzie et al. | |
| 6,524,251 B2 | 2/2003 | Rabiner et al. | |
| 6,524,300 B2 | 2/2003 | Meglin | |
| 6,542,767 B1 | 4/2003 | McNichols et al. | |
| 6,542,797 B2 | 4/2003 | Lohmiller | |
| 6,551,337 B1 | 4/2003 | Rabiner et al. | |
| 6,554,801 B1 | 4/2003 | Steward et al. | |
| 6,562,021 B1 | 5/2003 | Derbin et al. | |
| 6,582,392 B1 | 6/2003 | Bennett et al. | |
| 6,589,182 B1 | 7/2003 | Loftman et al. | |
| 6,599,288 B2 | 7/2003 | Maguire et al. | |
| 6,607,502 B1 | 8/2003 | Maguire et al. | |
| 6,647,755 B2 | 11/2003 | Rabiner et al. | |
| 6,652,547 B2 | 11/2003 | Rabiner et al. | |
| 6,660,013 B2 | 12/2003 | Rabiner et al. | |
| 6,663,613 B1 | 12/2003 | Evans et al. | |
| 6,676,626 B1 | 1/2004 | Bennett et al. | |
| 6,692,494 B1 | 2/2004 | Cooper et al. | |
| 6,711,953 B2 | 3/2004 | Hayashi et al. | |
| 6,723,063 B1 | 4/2004 | Zhang et al. | |
| 6,740,040 B1 | 5/2004 | Mandrusov et al. | |
| 6,824,515 B2 | 11/2004 | Suorsa et al. | |
| 6,855,123 B2 | 2/2005 | Nita | |
| 6,979,293 B2 | 12/2005 | Hansmann et al. | |
| 7,089,063 B2 | 8/2006 | Lesh et al. | |
| 2001/0037106 A1 | 11/2001 | Shadduck | |
| 2002/0000763 A1 | 1/2002 | Jones | |
| 2002/0022833 A1 | 2/2002 | Maguire et al. | |
| 2002/0032394 A1 | 3/2002 | Brisken et al. | |
| 2002/0133111 A1 | 9/2002 | Shadduck | |
| 2002/0151825 A1 | 10/2002 | Rubenchik et al. | |
| 2002/0161325 A1 | 10/2002 | Hansmann | |
| 2003/0023261 A1 | 1/2003 | Tomaschko et al. | |
| 2003/0028173 A1 | 2/2003 | Forsberg | |

| | | | |
|---|---|---|---|
| 2003/0036705 A1 | 2/2003 | Hare et al. | |
| 2003/0040698 A1 | 2/2003 | Makin et al. | |
| 2003/0069590 A1 | 4/2003 | Rabiner et al. | |
| 2003/0109812 A1 | 6/2003 | Corl et al. | |
| 2003/0236539 A1 | 12/2003 | Rabiner et al. | |
| 2004/0015061 A1 | 1/2004 | Currier et al. | |
| 2004/0015084 A1 | 1/2004 | Flesch et al. | |
| 2004/0015138 A1 | 1/2004 | Currier et al. | |
| 2004/0019318 A1 | 1/2004 | Wilson et al. | |
| 2004/0024347 A1 | 2/2004 | Wilson et al. | |
| 2004/0024393 A1 | 2/2004 | Nita et al. | |
| 2004/0039311 A1 | 2/2004 | Nita et al. | |
| 2004/0049148 A1 | 3/2004 | Rodriguez et al. | |
| 2004/0068189 A1 | 4/2004 | Wilson et al. | |
| 2004/0199228 A1 | 10/2004 | Wilson | |
| 2005/0215942 A1 | 9/2005 | Abrahamson et al. | |

FOREIGN PATENT DOCUMENTS

| | | |
|---|---|---|
| EP | 0 629 382 | 12/1994 |
| EP | 1 103 281 | 5/2001 |
| JP | H02-180275 | 7/1990 |
| WO | WO 89/04142 | 5/1989 |
| WO | WO 92/11815 | 7/1992 |
| WO | WO 93/16646 | 9/1993 |
| WO | WO 95/01751 | 1/1995 |
| WO | WO 95/09571 | 4/1995 |
| WO | WO 95/26777 | 10/1995 |
| WO | WO 96/29935 | 10/1996 |
| WO | WO 97/19644 | 6/1997 |
| WO | WO 97/19645 | 6/1997 |
| WO | WO 98/48711 | 11/1998 |
| WO | WO 98/56462 | 12/1998 |
| WO | WO 99/16360 | 4/1999 |
| WO | WO 00/00095 | 1/2000 |
| WO | WO 00/38580 | 7/2000 |
| WO | WO 01/13357 | 2/2001 |
| WO | WO 01/54754 | 8/2001 |
| WO | WO 03/030751 | 4/2003 |
| WO | WO 03/051208 | 6/2003 |
| WO | WO 2004/007012 | 1/2004 |
| WO | WO 2004/012609 | 2/2004 |

OTHER PUBLICATIONS

Lee et al.; "Array of Multielement Ultrasound Applicators for Interstitial Hyperthermia"; IEEE Transactions on Biomedical Engineering; vol. 46, No. 7; Jul. 1999.

International Search Report from PCT Application PCT/US04/12362, mailed Apr. 10, 2006.

* cited by examiner

US 7,993,308 B2

ULTRASOUND ENHANCED CENTRAL VENOUS CATHETER

PRIORITY CLAIM

This application is a continuation of U.S. patent application Ser. No. 10/828,938 (filed 21 Apr. 2004), which claims the benefit of U.S. Provisional Application 60/464,673 (filed 22 Apr. 2003), the entire disclosure of which is hereby incorporated in its entirety by reference herein.

FIELD OF THE INVENTION

The present invention relates generally to use of an ultrasound assembly with a central venous catheter, and more specifically to using ultrasonic energy to enhance the efficacy of a central venous catheter.

BACKGROUND OF THE INVENTION

The term "central venous catheter" or "CVC," refers generally, in addition to its ordinary meaning, to a catheter that has been inserted into a vein of the vascular system. Although CVCs have many varied applications, CVCs are frequently used when a patent requires frequent or continuous injections of medications or fluids for nutritional support. Common CVC applications include, but are not limited to, chemotherapy, long-term intravenous antibiotics, long-term pain medications, long-term intravenous nutrition, frequent blood draws, dialysis, and plasmapheresis. Therefore, a CVC can be used to deliver fluids to, or extract fluids from, the cardiovascular system.

In a wide variety of medical applications, the tip of a CVC is advanced into the superior vena cava ("SVC") from an upper extremity jugular vein or subclavian vein. Other approaches and deployment locations can be used in other applications. CVCs are used in a wide variety of applications; one common application is in the provision of a therapeutic compound into a patient's vascular system.

When a CVC is used for an extended period, blockages can form within the CVC, or can form outside the CVC in the vein between the CVC and the blood vessel wall. For example, a blockage inside the CVC can be caused by drug precipitate or thrombus. Additionally, platelet aggregation or fibrin deposition can completely encase the surface of the CVC, or can form a sac around the distal end of the CVC. Conventionally, such blockages were removed, if at all, either by removing and replacing/cleaning the CVC or while the CVC is in place passing a clot-dissolving compound through the CVC to dissolve the blockage. However, removing the CVC catheter is generally not desirable and introducing a large quantity of clot-dissolving compounds into the vascular system can have negative side effects.

SUMMARY OF THE INVENTION

Therefore, a device capable of removing blockages or other materials from within or around a CVC, without removing the CVC and/or causing the negative side effects associated with the introduction of large quantities of clot-dissolving compounds into the vascular system, has been developed. In addition, an improved CVC that is capable of being outfitted with an ultrasound assembly is also provided.

Accordingly, one embodiment of the present invention comprises an elongate central venous catheter. The elongate central venous catheter having a distal region configured for insertion into a patient's vasculature. The elongate central venous catheter also has a fluid delivery lumen configured to allow a fluid to be delivered through the central venous catheter to the patient's vasculature. The apparatus further comprises an ultrasound assembly configured to be positioned adjacent to the central venous catheter distal region. The apparatus further comprises a temperature sensor configured to measure a temperature in a region adjacent to the ultrasound assembly.

According to one embodiment of the present invention, a method for removing a blockage from a central venous catheter comprises inserting an ultrasound assembly into a central venous catheter. The ultrasound assembly comprises an ultrasound radiating member mounted on an elongate support structure. The method further comprises positioning the ultrasound assembly within the central venous catheter such that the ultrasound radiating member is adjacent to a deposited material formed on a portion of the central venous catheter. The method further comprises supplying an electrical current to the ultrasound radiating member to expose the deposited material to ultrasonic energy. The method further comprises passing a blockage removal compound through the central venous catheter to expose the deposited material to the blockage removal compound simultaneously with ultrasonic energy.

According to another embodiment of the present invention, a method comprises exposing a deposited material formed on a central venous catheter to ultrasonic energy while the central venous catheter is positioned in a patient and exposing the deposited material to a blockage removal compound while the central venous catheter is positioned in a patient.

According to another embodiment of the present invention, a method for removing a deposited material from a catheter comprises supplying a blockage removal compound to the deposited material. The method further comprises exposing the deposited material to ultrasonic energy generated by an ultrasound radiating member positioned within the catheter. The method further comprises measuring a temperature on the catheter to provide an indication of progression of the removal of the deposited material from the catheter.

BRIEF DESCRIPTION OF THE INVENTION

Exemplary embodiments of the CVCs disclosed herein, and exemplary methods for using said CVCs are illustrated in the accompanying drawings, which are for illustrative purposes only. The drawings comprise the following figures, in which like numerals indicate like parts.

DETAILED DESCRIPTION OF THE PREFERRED EMBODIMENTS

As described above, material can be deposited in and around a CVC during extended use. Such deposition can adversely affect operation of the CVC, making it difficult or impossible to deliver therapeutic compounds or other materials through the CVC to the patient's vasculature. Therefore, improvements have been developed to mitigate the adverse affects associated with material deposition in or around a CVC. Exemplary embodiments of these improvements are disclosed herein.

A wide variety of CVC structures exist, and the improvements described herein are not intended to be limited to a particular CVC structure. Rather, the improvements are described in connection with a generic CVC structure, with the understanding that these improvements are not limited to use with that particular CVC structure. For example, CVCs can be configured with multiple lumens, rather than a single central lumen. For example, in one embodiment, a CVC catheter has been one lumen and five lumens. Multiple lumens can be used for introducing and withdrawing fluids and devices, such as a guidewire. Likewise, the improvements disclosed herein can be used with catheters other than CVC catheters, such as with catheters configured to be inserted into other regions of the vascular system.

Accordingly, the term "central venous catheter" refers generally, in addition to its ordinary meaning, to a catheter that has been inserted into a vein of the vascular system. In a wide variety of medical applications, the tip of a CVC is advanced into the superior vena cava ("SVC") from an upper extremity jugular vein or subclavian vein. Other approaches and deployment locations can be used in other applications. CVCs are used in a wide variety of applications; one common application is in the provision of a therapeutic compound into a patient's vascular system.

As used herein, the term "therapeutic compound" refers broadly, without limitation, to a drug, medicament, dissolution compound, genetic material or any other substance capable of effecting physiological functions. Additionally, any mixture comprising any such substances is encompassed within this definition of "therapeutic compound", as well as any substance falling within the ordinary meaning of these terms.

As used herein, the term "ultrasound energy" is a broad term and is used in its ordinary sense and means, without limitation, mechanical energy transferred through pressure or compression waves with a frequency greater than about 20 kHz. In one embodiment, the waves of the ultrasound energy have a frequency between about 500 kHz and 20 MHz and in another embodiment between about 1 MHz and 3 MHz. In yet another embodiment, the waves of the ultrasound energy have a frequency of about 3 MHz.

As used herein, the term "catheter" is a broad term and is used in its ordinary sense and means, without limitation, an elongate flexible tube configured to be inserted into the body of a patient, such as, for example, a body cavity, duct or vessel.

Figure 1:
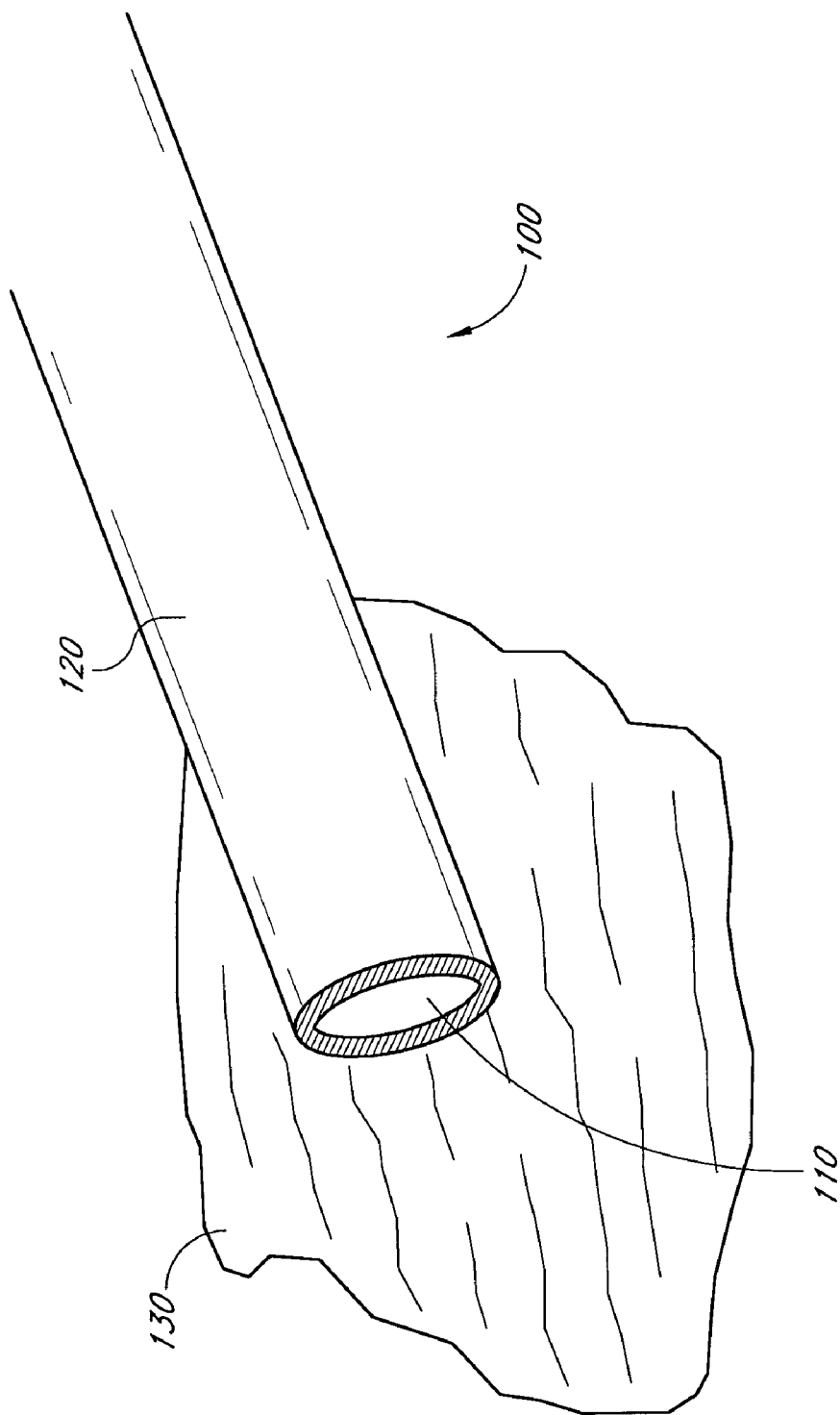
FIG. 1 is a perspective view of an exemplary embodiment of a distal end of a CVC structure having a fibrin sleeve formed thereover.
Figure 2:
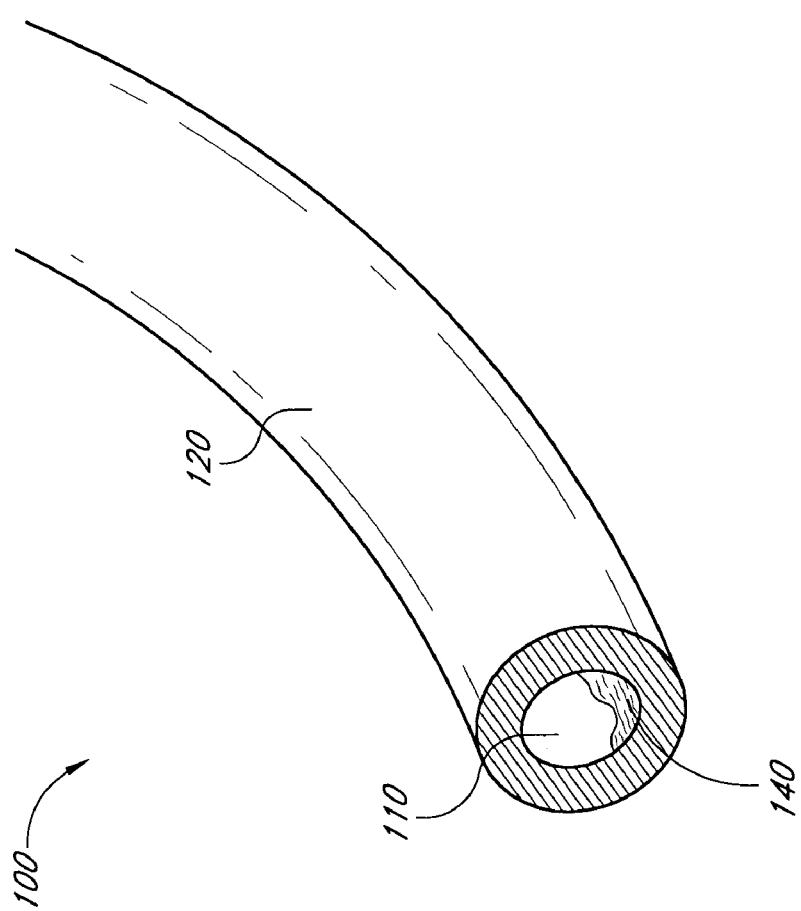
FIG. 2 is a perspective view of an exemplary embodiment of a distal end of a CVC structure having a intraluminal thrombus or clot formed therein.

A distal region of a generic CVC structure is illustrated in FIGS. 1 and 2. As illustrated, a generic CVC comprises a flexible, elongate body 100 that forms a central lumen 110. The elongate body 100 has an outer surface 120, and is dimensioned to facilitate its passage through the peripheral vascular system. Generally, suitable materials and dimensions for the CVC can be selected readily based on the natural and anatomical dimensions of the particular treatment site and percutaneous access site. Examples of suitable CVC materials include, but are not limited to, extruded polytetrafluoroethylene ("PTFE"), polyethylenes ("PE"), polyamides and other similar materials. In CVCs configured for long term implantation, soft materials such as urethanes and silicones can be used to form the catheter body. Additionally, a CVC optionally includes a coating, such as a silver coating, to reduce the likelihood of infection.

In certain embodiments, the proximal region of the CVC is reinforced by braiding, mesh or other internal or external structures to provide increased kink resistance and pushability, thereby facilitating passage of the CVC through the patient's vasculature. In other embodiments, the CVC body can be reinforced by including a stylet in the CVC body, which serves to maintain rigidity of the CVC during passage through the patient's vasculature. In such embodiments, a thin, elongate wire can be used as a stylet.

In one embodiment, a CVC has an outer diameter between approximately 6 French and approximately 14 French.

Figure 6:
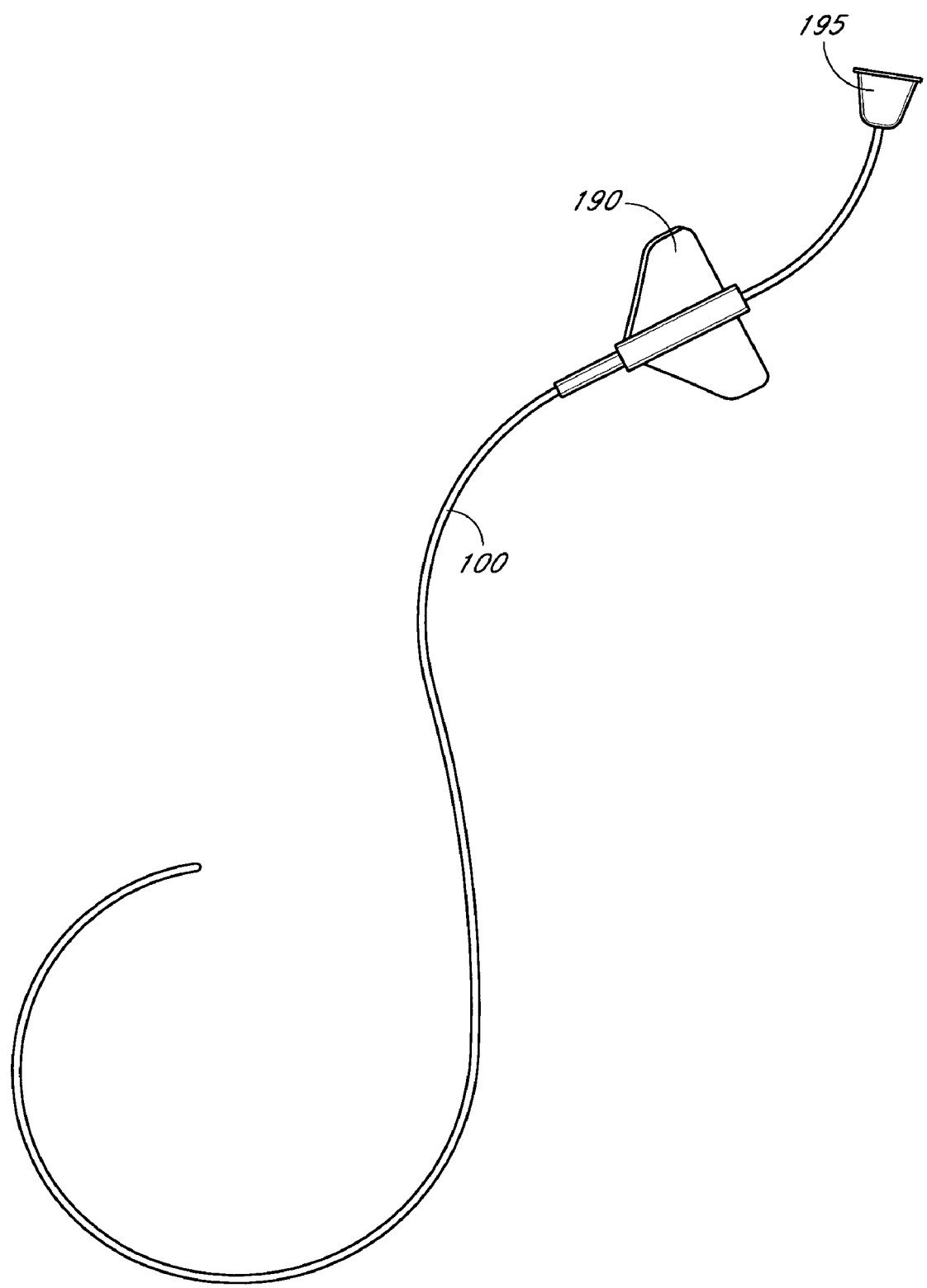
FIG. 6 is a perspective illustration of a CVC elongate body having a suture wing in the catheter proximal region.

A CVC optionally includes a suture wing or cuff in the catheter proximal region, which can be used to attach the proximal end of the CVC to the patient. For example, FIG. 6 illustrates a CVC elongate body 100 having a suture wing 190 in the catheter proximal region. The suture wing 190 can be constructed of a material suitable for attachment to a patient's body. In other embodiments, a cuff that may be made out of a material such as Dacron can be used. As illustrated, the CVC optionally includes a proximal hub 195 that can be used to supply fluid, such as a therapeutic compound, through a CVC lumen.

As described above, material often deposits in and around a CVC that has been positioned within a patent's vasculature for an extended period of time. Such blockages can be caused by therapeutic compound precipitate, platelet aggregation, or fibrin deposition. For example, FIG. 1 illustrates the formation of a fibrin sleeve 130 at the distal region of the CVC, and FIG. 2 illustrates the formation of a thrombus or clot 140 within the CVC central lumen 110. Either of these conditions can adversely affect the operation of the CVC, making it difficult or impossible to pass therapeutic compounds or other materials through the CVC and into the patient's vasculature.

The blockages described above, whether formed inside or outside the CVC, often become coated with a protein substance that provides a shield for bacteria. This protein "shield" makes it difficult to treat bacterial growth within the blockage using antibiotics. Therefore, because of the bacteria-resistant shield, bacterial growth within the blockage can proliferate, increase the size of the blockage, and cause infection. This process is a significant contributing factor to upper extremity deep vein thrombosis ("DVT").

An obstruction within a CVC can be cleaned while in the patient by using a brush and a small amount of a therapeutic compound, such as a lytic solution. However, it is difficult or impossible to clean the outer surface of a CVC using a brush. In an exemplary embodiment, ultrasonic energy is used to clean one or more portions of a CVC, such as the central lumen 110, the elongate body outer surface 120, or both. Preferably, the ultrasonic energy is used in combination with a blockage removal compound to clean the one or more portions of the CVC. In such embodiments, the ultrasonic energy is preferably configured to enhance the therapeutic effects and/or delivery of the blockage removal compound. For example, the ultrasonic energy can be used to penetrate the protein shield that often covers an occlusion, thereby allowing a blockage removal compound, such as a solution containing an antibacterial agent and/or a thrombus removing compound (e.g., Heparin, Uronkinase, Streptokinase, TPA and other thrombolytics or anti-thrombus agents) to be delivered directly to the occlusion. The ultrasonic energy can be delivered independent of, or simultaneously with, the blockage removal compound. In another use of the system disclosed herein, a CVC is exposed to ultrasonic energy periodically to reduce or prevent accumulation of protein thereon.

Preferably, in these embodiments, the ultrasound and/or the blockage removal compound applied while the central venous catheter is positioned in a patient.

Figure 3:
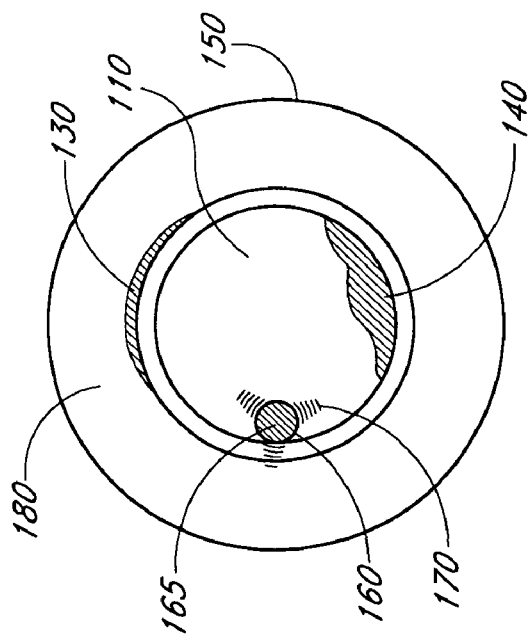
FIG. 3 is a cross-sectional view of a CVC disposed within a patient's vasculature, wherein an ultrasound assembly is positioned within the CVC.

One system for using ultrasonic energy to clean a CVC is illustrated in FIG. 3. FIG. 3 is a cross-sectional illustration of the elongate body 100 of a CVC that has been positioned within a patient's vasculature 150. As illustrated, this system can be used to clean deposited material from within the CVC outer surface 120 (such as a fibrin sleeve 130), or from the CVC inner lumen 110 (such as a thrombus or clot 140), or both. Similarly, this system can be used to clean deposited material from the distal end of the CVC, or from an intermediate position on the CVC.

Figure 4:
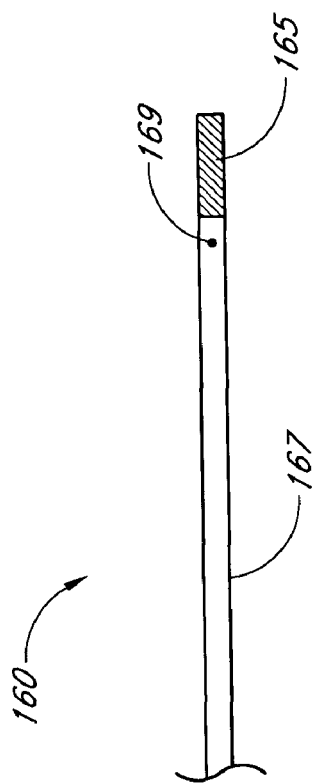
FIG. 4 is a side view of the ultrasound assembly positioned within the CVC of FIG. 3.

Still referring to FIG. 3, to expose the deposited material to ultrasonic energy, an ultrasound assembly 160 is inserted into, and passed through the elongate body 100. The ultrasound assembly 160, a side view of which is illustrated in FIG. 4, comprises an ultrasound radiating member 165 positioned at the distal end of an elongate support member 167. In an exemplary embodiment, the ultrasound radiating member comprises lead zirconate titanate ("PZT"), although other materials capable of generating mechanical vibrations when exposed to electronic signals can also be used. Although the ultrasound assembly 160 illustrated in FIG. 4 comprises one ultrasound radiating member 165, in a modified embodiment, multiple ultrasound radiating members are positioned along the elongate support member 167. The multiple ultrasound radiating members can be controlled independently of each other. In another modified embodiment, the ultrasound radiating member is mechanically connected to an ultrasound oscillator positioned at the proximal end of the CVC, outside the patient's body; additional information regarding this configuration is provided U.S. Pat. No. 6,524,251, issued on 25 Feb. 2003, and entitled "Ultrasonic Device for Tissue Ablation and Sheath for Use Therewith."

Additional information regarding controlling a plurality of ultrasound radiating members are provided in U.S. patent application Publication US 2004/0024347 A1, published on 5 Feb. 2004 and entitled "Catheter with Multiple Ultrasound Radiating Members," the entire disclosure of which is hereby incorporated herein by reference herein. Additional information regarding mounting one or more ultrasound radiating members on an elongate support structure are provided in U.S. patent application Ser. No. 10/751,843, filed on 5 Jan. 2004 and entitled "Ultrasonic Catheter with Axial Energy Field," the entire disclosure of which is hereby incorporated by reference herein.

A temperature sensor 169 is optionally positioned in a distal region of the elongate support member 169. In other embodiments, the temperature sensor 169 is positioned directly on the ultrasound radiating member 165. In such embodiments, the ultrasound radiating member 165, and optionally the temperature sensor 169, are electrically connected to control circuitry at a proximal end of the ultrasound assembly 160. The temperature sensor can be used to monitor and control the progression of the cleaning procedure. In particular, when removing a blockage from within or around a CVC, a decrease in the temperature at the treatment site can indicate that the blockage has been at least partially removed or dissolved, and that flow has been at least partially reestablished at the treatment site. In addition, the temperature sensor may be used to determine that the radiating member is positioned 165 within the blockage. Additional information regarding using temperature measurements to monitor the progression of an ultrasound-enhanced treatment are provided in U.S. patent application Publication 2003/0220568 A1, published on 27 Nov. 2003 and entitled "Blood Flow Reestablishment Determination," as well as in U.S. Provisional Patent Applications 60/540,900 (filed 29 Jan. 2004) and 60/540,703 (filed 30 Jan. 2004); the entire disclosure of these three applications is hereby incorporated by reference herein.

As described above, the ultrasound assembly 160 is passed through the CVC to a point that the ultrasound radiating member 165 is positioned adjacent to a blockage. The blockage is located either within the CVC elongate body 100, or outside the CVC elongate body 100. When the ultrasound radiating member 165 is activated via the control circuitry, ultrasonic vibrations are generated, thereby exposing the blockage to ultrasonic energy 170. The blockage can also optionally be exposed to a blockage removal compound to assist in breaking down or dissolving the blockage, such as a thrombolytic solution or an antibacterial solution. The blockage removal compound can be delivered through the CVC itself, or can be independently supplied to the treatment site by, for example, a secondary delivery catheter or a delivery lumen formed integrally with the central venous catheter. In an exemplary embodiment, the ultrasonic energy enhances the effect of the blockage removal compound, as described previously.

In a modified embodiment, the CVC is configured to facilitate the delivery of ultrasonic energy to blockages that form on or within the elongate body. For example, in one embodiment, the elongate body, or optionally only a distal region of the elongate body, is formed from a material that is substantially transparent to ultrasonic energy. This configuration advantageously allows ultrasonic energy generated by an ultrasound radiating member positioned within the central lumen 110 to pass through the elongate body 100 and be absorbed by a blockage outside the CVC.

The ultrasound radiating member 165 need not be positioned within the CVC central lumen 110. For example, the ultrasound assembly can be passed along the outer surface 120 of the CVC in a region 180 (see FIG. 3) between the patient's vasculature 150 and the CVC. In another embodiment, the ultrasound radiating member 150 is embedded within the walls of the CVC, as illustrated in FIGS. 5A and 5B.

Figure 5A:
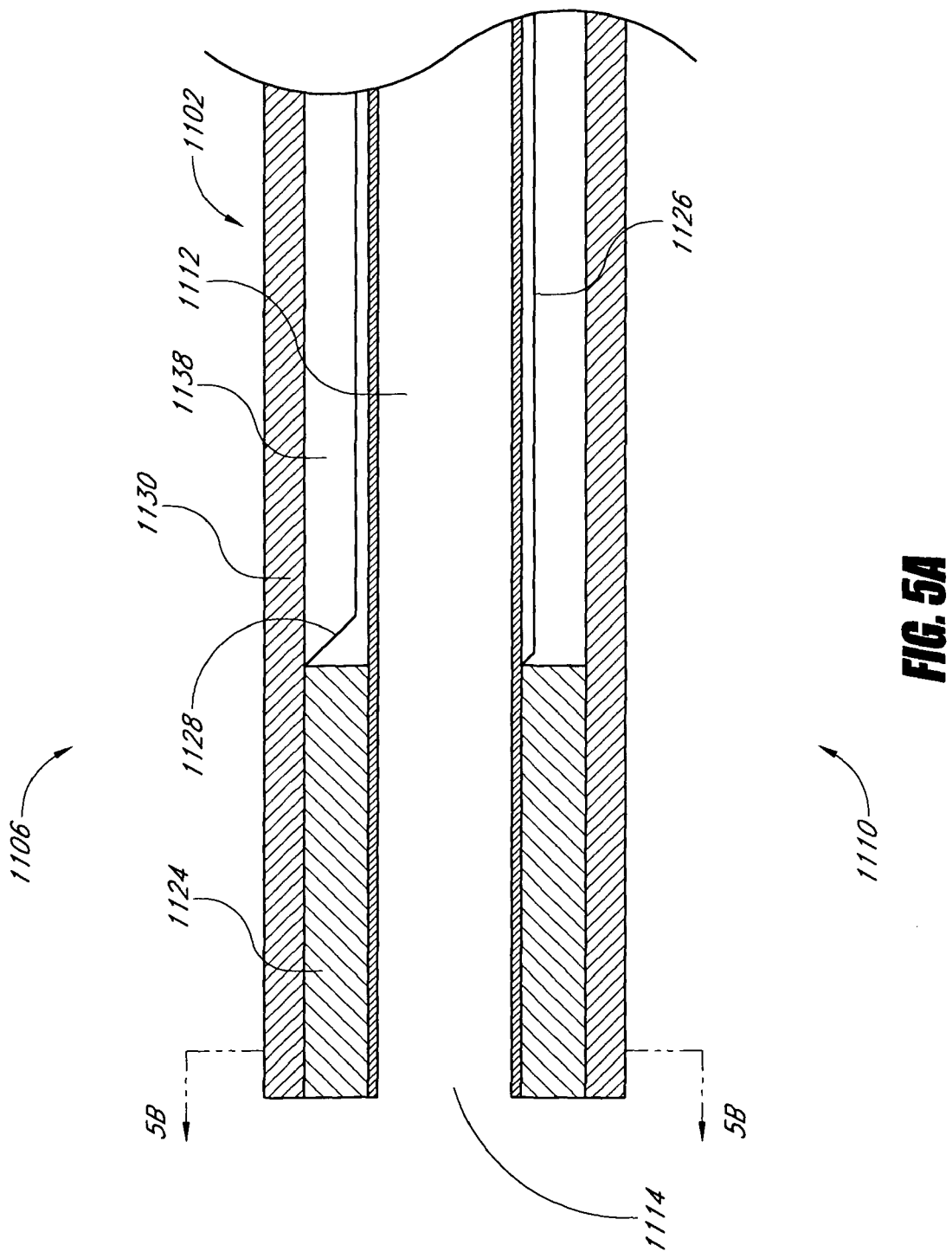
FIG. 5A is a cross-sectional view of a CVC having an embedded ultrasound radiating member.
Figure 5B:
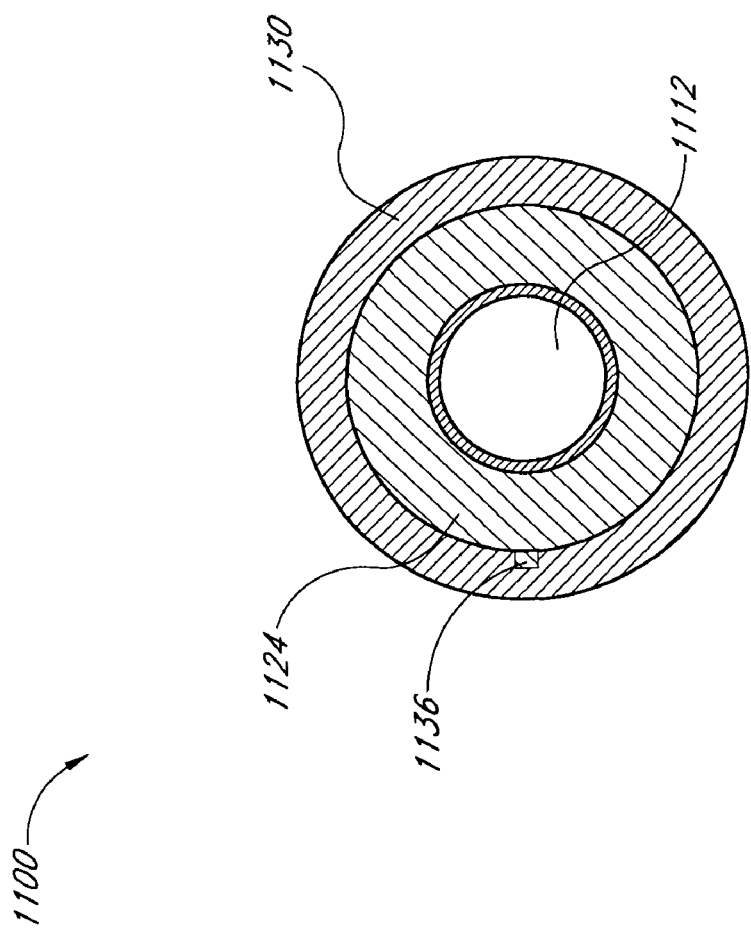
FIG. 5B is a cross-sectional view of the CVC of FIG. 5A, taken along line 5B-5B.

As shown in FIGS. 5A and 5B, a modified ultrasound catheter 1100, such as a CVC, generally comprises a multi-component tubular body 1102 having a proximal region (not shown) and a distal region 1106. Suitable materials and dimensions for the ultrasound catheter 1100 can be selected based on the natural and anatomical dimensions of the treatment site and of the percutaneous access site.

The elongate, flexible tubular body 1102 comprises an outer sheath 1130 that is positioned upon an inner core 1110. In an exemplary embodiment, the outer sheath 1130 comprises extruded PEBAX, PTFE, PEEK, PE, polymides, braided polymides and/or other similar materials that are substantially transparent to ultrasonic energy. In an exemplary embodiment, the inner core 1110 comprises polymide or a similar material which, in some embodiments, can be braided to increase the flexibility of the tubular body 1102. The inner core 1110 at least partially defines a delivery lumen 1112 that extends longitudinally along the catheter 1100. The delivery lumen 1112 includes a distal exit port 1114. At a proximal end of the catheter 1100, the delivery lumen 1112 optionally includes a Luer fitting to facilitate the passage of a fluid therethrough.

Still referring to the exemplary embodiment illustrated in FIGS. 5A and 5B, the tubular body distal region 1106 includes the ultrasound radiating member 1124. In a modified embodiment, the ultrasonic energy can be generated by an ultrasound radiating member that is remote from the treatment site; in such embodiments the ultrasonic energy can be transmitted via, for example, a wire to the treatment site, as described above.

As illustrated in FIGS. 5A and 5B, the ultrasound radiating member 1124 is configured as a hollow cylinder. As such, the inner core 1110 extends through the ultrasound radiating member 1124. The ultrasound radiating member 1124 is secured to the inner core 1110 in a suitable manner, such as with an adhesive. A potting material is optionally used to further secure the mounting of the ultrasound radiating member 1124 along the inner core 1110.

In other embodiments, the ultrasound radiating member 1124 is configured with a different shape. For example, the ultrasound radiating member can be configured as a solid rod, a disk, a solid rectangle, a curved element (such as a split cylinder or a curved rectangular element), or a thin block. In such embodiments the ultrasound radiating members are configured with dimensions that allow them to be embedded within the walls of the CVC, as the ultrasound radiating member 1124 illustrated in FIGS. 5A and 5B is embedded in the CVC wall. In other embodiments, wherein the CVC includes a plurality of lumens formed within the catheter, the ultrasound radiating members can be embedded in the catheter walls between the lumens. Because relatively soft materials are often used to form the CVC body, as described above, the catheter walls can be configured with a relatively large thickness, thereby providing ample space to support one or more embedded ultrasound radiating members. Particular characteristics of the ultrasound radiating member can be optimized with routine experimentation based on the particular physical configuration of the CVC body, including the CVC body materials, dimensions, and shape.

Still further, the ultrasound radiating member can comprise a plurality of smaller ultrasound radiating members. However, the illustrated arrangement advantageously provides for enhanced cooling of the ultrasound radiating member 1124. For example, in embodiments wherein a therapeutic compound is delivered through the delivery lumen 1112, the therapeutic compound advantageously serves as a heat sink for removing heat generated by the ultrasound radiating member 1124. In another embodiment, a return path can be formed in the region 1138 between the outer sheath 1130 and the inner core 1110, such that coolant from a coolant system can be directed through the region 1138.

In a modified embodiment, the CVC is configured to caused the ultrasonic energy generated by the ultrasound radiating member to radiate outward from the CVC or inward toward the central lumen. This can be accomplished, for example, by positioning a chamber of high ultrasonic impedance material on the opposite side of the ultrasound radiating member from where the ultrasonic energy is to be directed. This modification can be made with a variety of different ultrasound radiating member configurations, including hollow cylindrical configurations and rectangular configurations. Additional information regarding the use of a backing to direct ultrasonic energy is provided is U.S. Pat. No. 6,676,626, issued on 13 Jan. 2004, and entitled "Ultrasound Assembly with Increased Efficacy," and in U.S. Pat. No. 6,582,392, issued on 24 Jun. 2003, and entitled "Ultrasound Assembly for Use with a Catheter", which are hereby incorporated by reference herein in their entirety.

In an exemplary embodiment, the ultrasound radiating member 1124 is selected to produce ultrasonic energy in a frequency range that is well suited for removal of deposited material from the catheter 1100. Suitable frequencies of ultrasonic energy include, but are not limited to, from about 20 kHz to about 20 MHz. In one embodiment, the frequency is between about 500 kHz and 20 MHz, and in another embodiment the frequency is between about 1 MHz and about 3 MHz. In yet another embodiment, the ultrasonic energy has a frequency of about 3 MHz.

As described above, ultrasonic energy is generated from electrical power supplied to the ultrasound radiating member 1124. The electrical power can be supplied through a pair wires 1126, 1128 that extend through the tubular body 1102. In an exemplary embodiment, the electrical wires 1126, 1128 are secured to the inner core 1110, lay along the inner core 1110, and/or extend freely in the region 1138 between the inner core 1110 and the outer sheath 1130. In the illustrated arrangement, the first wire 1126 is connected to the hollow center of the ultrasound radiating member 1124, while the second wire 1128 is connected to the outer periphery of the ultrasound radiating member 1124.

With continued reference to the exemplary embodiment illustrated in FIG. 5B, the catheter 1100 includes at least one temperature sensor 1136 along the tubular body distal region 1106. The temperature sensor 1136 is located on or near the ultrasound radiating element 1124. Suitable temperature sensors include but are not limited to, diodes, thermistors, thermocouples, resistance temperature detectors ("RTDs"), and fiber optic temperature sensors that used thermalchromic liquid crystals. In such embodiments, the temperature sensor is operatively connected to control circuitry through a control wire that extends through the tubular body 1102.

In other embodiments, a vibrational element is embedded in the wall of a CVC. In such embodiments, the vibrational element comprises a metallic compound that can be vibrated by application of an oscillating electromagnetic field from outside the body. For example, an externally-applied electromagnetic field can be used to vibrate a ferro-metallic ring or cylinder embedded in the wall of the catheter 1100. In such embodiments, wires and electrodes used to supply power to an ultrasound radiating member can be eliminated. In certain embodiments, the vibrational element embedded is configured to vibrate upon application of an externally-applied oscillating electric field, or magnetic field, or upon application of externally-applied ultrasonic energy.

Scope of the Invention

For purposes of describing the invention and the advantages achieved over the prior art, certain features, objects and advantages of the invention have been set forth herein. Not necessarily all such features, objects or advantages may be used or achieved in accordance with a particular embodiment of the invention. Thus, for example, the invention may be embodied or carried out in a manner that achieves or optimizes one advantage or group of advantages as taught herein without necessarily achieving other objects or advantages as may be taught or suggested herein. In addition, various methods and procedures have been described above. It should be understood that those methods and procedures should not be limited to the sequence described but may be performed in different orders and that not necessarily all of the steps of a method or procedure needs to be performed. Furthermore, the present invention is not limited to any particular disclosed embodiment, but is limited only by the claims set forth below.

We claim:

1. A method for removing a blockage from a central venous catheter comprising:
   inserting an ultrasound assembly into a central venous catheter positioned in a patient, the ultrasound assembly comprising an ultrasound radiating member mounted on an elongate support structure;

positioning the ultrasound assembly within the central venous catheter positioned in a patient such that the ultrasound radiating member is adjacent to a deposited material formed on a portion of the central venous catheter;

supplying an electrical current to the ultrasound radiating member to expose the deposited material to ultrasonic energy while the central venous catheter is positioned in a patient; and passing a blockage removal compound through the central venous catheter to expose the deposited material to the blockage removal compound simultaneously with ultrasonic energy.

2. The method of claim 1, wherein the ultrasound assembly comprises a plurality of ultrasound radiating members.

3. The method of claim 1, wherein the ultrasound assembly comprises a plurality of ultrasound radiating members, and wherein the plurality of ultrasound radiating members are individually controllable.

4. The method of claim 1, further comprising measuring a temperature in a region adjacent to the ultrasound radiating member.

5. The method of claim 1, further comprising:
measuring a temperature in a region adjacent to the ultrasound radiating member; and
adjusting the electrical current supplied to the ultrasound radiating member based on the measured temperature.

6. The method of claim 1, wherein the blockage removal compound is also passed through the central venous catheter before ultrasonic energy is supplied to the deposited material.

7. A method comprising exposing a deposited material formed on a central venous catheter to ultrasonic energy while the central venous catheter is positioned in a patient and exposing the deposited material formed on the central venous catheter to a blockage removal compound while the central venous catheter is positioned in a patient.

8. The method of claim 7, wherein the blockage removal compound comprises an antibacterial solution.

9. The method of claim 7, wherein the ultrasonic energy has a frequency between about 20 kHz and about 20 MHz.

10. The method of claim 7, the blockage removal compound comprises a thrombus removing agent.

11. The method of claim 7, wherein the blockage removal compound is also delivered to the deposited material before ultrasonic energy is supplied to the deposited material.

12. The method of claim 7, wherein the ultrasonic energy is also delivered to the deposited material after termination of the delivery of blockage removal compound to the deposited material.

13. The method of claim 7, wherein the ultrasonic energy is delivered from an ultrasound assembly positioned within a central lumen of the central venous catheter.

14. The method of claim 7, wherein the ultrasonic energy is delivered from an ultrasound assembly positioned within a central lumen of the central venous catheter, and wherein the ultrasound assembly comprises an ultrasound radiating member mounted on an elongate support structure.

15. The method of claim 7, wherein the ultrasonic energy is delivered from an ultrasound assembly positioned within a central lumen of the central venous catheter, and wherein the ultrasound assembly comprises a plurality of ultrasound radiating members mounted on an elongate support structure.

16. The method of claim 7, further comprising measuring a temperature adjacent to the deposited material.

17. The method of claim 7, further comprising:
measuring a temperature adjacent to the deposited material; and
adjusting the amount of ultrasonic energy delivered to the deposited material based on the measured temperature.

18. The method of claim 7, wherein the ultrasonic energy is delivered from an ultrasound radiating member embedded in an elongate body of the central venous catheter.

19. The method of claim 7, wherein the blockage removal compound is delivered to the deposited material through the central venous catheter.

20. The method of claim 7, wherein the blockage removal compound is delivered to the deposited material through a delivery lumen formed integrally with the central venous catheter.

* * * * *